United States Patent [19]

Wittmann-Liebold et al.

[11] 3,986,521

[45] Oct. 19, 1976

[54] EVACUATION DEVICE

[75] Inventors: Brigitte Wittmann-Liebold; Horst Graffunder; Heinz Kohls, all of Berlin, Germany

[73] Assignee: Max-Planck-Gesellschaft zur Forderung der Wissenschaften e.V., Gottingen, Germany

[22] Filed: Mar. 10, 1975

[21] Appl. No.: 556,854

[30] Foreign Application Priority Data

Mar. 21, 1974 Germany............................ 2413704

[52] U.S. Cl.................................. 137/334; 34/92; 137/565; 137/599
[51] Int. Cl.² .............................................. F26B 5/04
[58] Field of Search ............ 34/5, 92; 137/334, 565, 137/599

[56] References Cited
UNITED STATES PATENTS

| | | | |
|---|---|---|---|
| 2,589,373 | 3/1952 | Hammock........................... | 137/599 |
| 3,018,561 | 1/1962 | Wells.................................. | 34/92 X |
| 3,126,902 | 3/1964 | Fite et al........................... | 137/334 X |
| 3,178,829 | 4/1965 | Cox..................................... | 34/5 |

Primary Examiner—Robert G. Nilson
Attorney, Agent, or Firm—Blum, Moscovitz, Friedman & Kaplan

[57] ABSTRACT

An evacuation device for removing volatile components from a reaction vessel of a protein sequenator and requiring connection to a single vacuum pump is provided. The evacuation device includes a vacuum path having a downstream end thereof connectable through a cooling trap to the vacuum pump and an upstream end defining an input. The vacuum path additionally includes a shutoff valve intermediate the length thereof. A further vacuum path bridges the first mentioned vacuum path upstream and downstream of the shutoff valve and has a smaller vacuum cross-section and houses a throttle therein, the second vacuum path being used for generating a prevacuum in response to the closing of the shutoff valve in the first mentioned vacuum path.

7 Claims, 2 Drawing Figures

EVACUATION DEVICE

BACKGROUND OF THE INVENTION

This invention relates generally to an evacuation device and especially to an evacuation device for removing volatile components from a reaction vessel of a protein sequenator.

Known evacuation devices for the reaction vessel of a protein sequenator have been characterized by first evacuation path including a first long and extremely narrow evacuation line acting as a throttle and including a shutoff valve. The first evacuation line discharges into a second evacuation line of wider cross-section also including a shutoff valve, the second vacuum path in turn discharging into a vacuum tank. The vacuum tank is evacuated by a first pump and is utilized as a vacuum reservoir for: producing suction in the reaction vessel over the first evacuation path; effecting evacuation of a fraction collector; and providing vacuum control for the pilot valves which valves open the actual dosing valves of a dosing device by pneumatic control of a diaphragm.

A second evacuation path having a larger cross-section is evacuated by a second vacuum pump and is sealed closed by an oil-sealed vacuum valve. Accordingly, over the first evacuation line, a first prevacuum builds up comparatively slowly, so that the skin of a substance contained in the reaction vessel and still in liquid form is not damaged by an extremely abrupt vacuum action thereon. Once the first prevacuum in the first evacuation line is effected, such line is closed to thereby apply the prevacuum over the second evacuation line. Thereafter, the second evacuation path is opened and utilized for generating a fine vacuum. Such a sequence of operation is required in order to separate the more vigorous vacuum functions from the less vigorous vacuum functions since otherwise the end vacuum is not sufficient to effect satisfactory drying of the film of the substance, particularly in the relatively short periods required to limit the program sequence of the reaction cycle.

It is noted that the reaction cycle in the reaction vessel cannot be effected unless two vacuum pumps are utilized. Additionally, solvent vapors drawn off by the suction from the evacuation device are directed to the vacuum pumps, causing same to settle and/or react with the oil that is needed for operating the pumps, thereby causing a rapid decline in the output and necessitating constant maintenance. Additionally it further renders it difficult to insure that identical conditions are maintained during successive reaction cycles. Moreover, the rapidly declining output of the pumps and the variable conditions during successive reaction cycles such as for example when the fraction collector has just been evacuated renders the prevacuum through the first evacuation line incapable of functioning within the time alloted for under the program, hence resulting in the substance film not being dried gently on the surface and deterioration of the substance film when the prevacuum is abruptly switched to the second evacuation line.

Still further problems occur because the substance deposits in the first evacuation path remain therein from cycle to cycle since the fine vacuum is incapable of eliminating same. Additionally the substance and solvent vapors remain deposited in large quantities in the vacuum tank thereby weakening the existing vacuum causing the results noted above as well as the improper control of the dosing valves by the pilot valves since pilot valves are operated in response to the strength of the vacuum measured thereby. Finally, if the diaphragm is damaged in any way, even a hairline crack, the active vapors will get into the pilot valves, thereby causing a disintegration of the rubber packing, such as by heptafluoride butyric acid and butane chloride, thereby diminishing the dosing in the reaction vessel hence causing heavy impurities to find their way into the reaction vessel.

SUMMARY OF THE INVENTION

Generally speaking, in accordance with the invention, an evacuation device for removing volatile components from a reaction vessel of a protein sequenator is provided. A vacuum path having a downstream end thereof is connectable through a cooling trap to a vacuum pump. A shutoff valve is included intermediate the length of the vacuum path. A further vacuum path bridges the first mentioned vacuum path upstream and downstream of the shutoff valve and is provided with a smaller vacuum cross-section than the first mentioned vacuum path, the further vacuum path being provided with a throttle therein and being used for generating a prevacuum in the reaction vessel in response to closing of the shutoff valve in the first mentioned vacuum path.

Accordingly, it is an object of this invention to provide an improved evacuation device wherein a single vacuum pump is required for completing a reaction cycle in a reaction vessel.

Still another object of this invention is to provide an evacuation device having a simplified design for improved operation and reduced maintenance.

Still a further object of this invention is to provide an evacuation device wherein identical operating conditions during successive reaction are insured.

Still other objects and advantages of the invention will in part be obvious and will in part be apparent from the specification and drawings.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
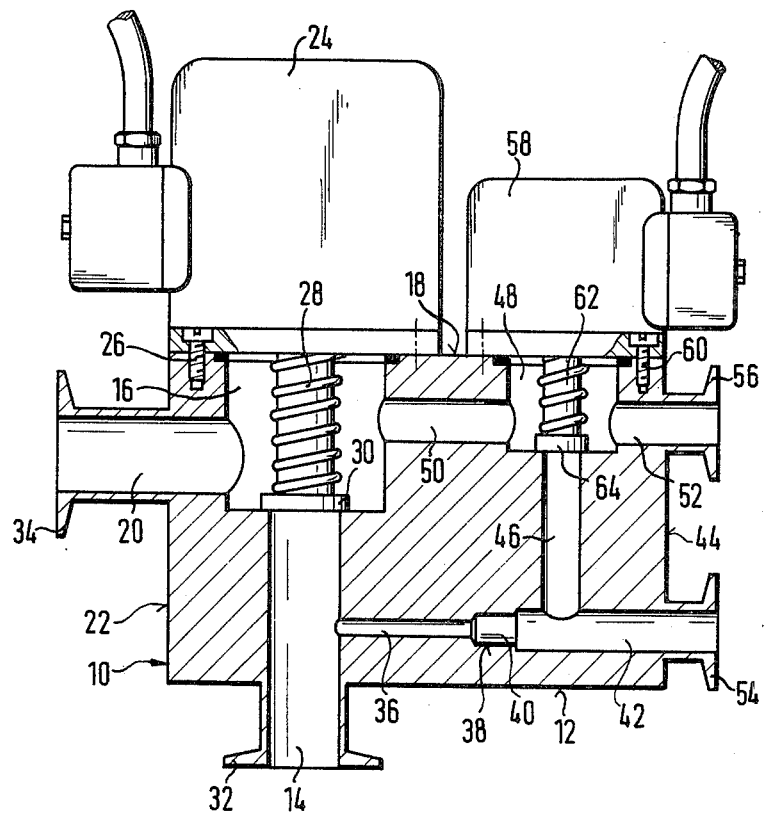
FIG. 1 is an elevational view, partly in section, of an evacuation device constructed in accordance with the invention.

Referring now to FIG. 1, an evacuation device for removing volatile components from films, solid deposits and the like is formed in a parallelelipiped block 10, which block serves as a connection member between a reaction vessel (not shown) and a vacuum pump (not shown). The block can be formed of aluminum, although other like metals can be utilized.

A first evacuation path in the block 10 is defined in part by borehole 14 which communicates an opening in the basal surface 12 to a coaxial valve chamber 16 of a larger diameter than the borehole 14. The first evacuation path further includes borehole 20 for communicating an opening in lateral surface 22 to valve chamber 16, borehole 20 being provided with the same diameter as borehole 14. Valve chamber 16 includes a main shutoff valve 24 occluding the valve chamber 16 and being secured thereto by screw 26, said valve by means of plunger 30 and biasing spring 28 being adapted to selectively seal borehole 14. Junction flanges 32 and 34 are respectively mounted on the openings of boreholes 14 and 20 to facilitate connection of borehole 14 to a reaction vessel and borehole 20 to a suction line which in turn is coupled to an evacuation pump. Thus, the first evacuation path leads from the reaction vessel through borehole 14, valve chamber 16 and borehole 20 to a vacuum pump.

A second evacuation path is adapted to bridge the point at which the shutoff valve plunger 30 seals the first evacuation path. A borehole 36 communicates borehole 14 through a throttle point 38 defined by a throttling nozzle 40 to a further borehole 42 defining an opening in lateral surface 44. The borehole 42 is disposed coaxial to borehole 36 and has a larger diameter than same. Disposed at a right angle to borehole 42 is a borehole 46 in communication with valve chamber 48, which chamber, like chamber 16 is occluded by auxiliary shutoff valve 58 mounted thereto by screws 60, and by use of spring 62 and plunger 64 is adapted to seal borehole 46. Finally, the second evacuation path includes borehole 50 which communicates valve chamber 48 with valve chamber 16 to effect a bridging of the first evacuation path by the second evacuation path comprised of borehole 36, throttling nozzle 40, borehole 42, valve chamber 48 and borehole 50. Additionally, borehole 50 extends through the valve chamber 48 to define a further opening in the lateral surface 44. Junction flanges 54 and 56 are respectively mounted on the cutaways of boreholes 42 and 52 for facilitating the joining of vacuum measuring tubes of the type utilized in vacuum measuring instruments.

Figure 2:
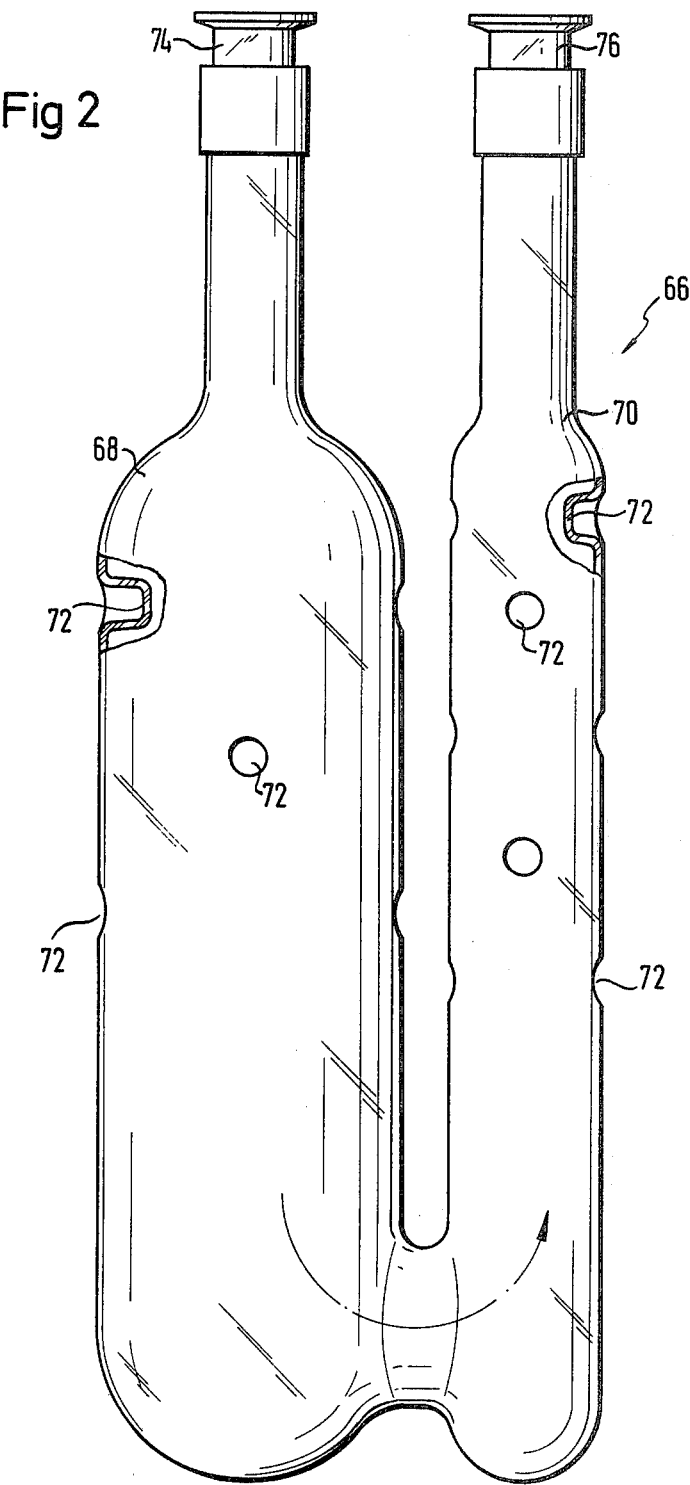
FIG. 2 is a elevational view, partly in section, of a cooling trap constructed in accordance with the instant invention and adapted for use in combination with the evacuation device depicted in FIG. 1.

Reference is made to FIG. 2, wherein a cooling trap 66 adapted to be inserted between a vacuum pump and the first evacuation path is depicted. The cooling trap is comprised of a vitreous U-tube, with bottle-shaped shanks 68 and 70. The walls of the shanks 68 and 70 form inwardly enlarged surface portions 72. Junction flanges 74 and 76 are respectively secured by a special adhesive to the ends of the U-shanks 68 and 70. Accordingly, the cooling trap can be cooled by well known techniques such as, for example, a vessel with liquid nitrogen. Moreover, it is noted, that all the junction flanges are vacuum flanges of standardized size and hence are easily joined to the standardized vacuum lines for suitable use in such evacuating devices.

When the evacuation device depicted in FIG. 1 is coupled through a cooling trap, such as the cooling trap depicted in FIG. 2, to a vacuum pump, the following evacuation procedure nozzle effected in a reaction vessel coupled to the borehole 14 at the input of the first evacuation path. Initially, the main shutoff valve 28 effects a seal of the first evacuation path by biasing plunger 30 to effect a closing of borehole 14. Additionally, auxiliary shutoff valve 58 maintains the second evacuation path open. Accordingly, a prevacuum is induced as a result of the opening of the auxiliary shutoff valve 58, and the pumped down gases flow through junction flange 32 into borehole 14, whereafter same is diverted through the open second evacuation path defined by borehole 36, throttle nozzle 40, borehole 42, borehole 46, valve chamber 48, borehole 50 and into valve chamber 16, whereafter same is directed to the cooling trap through the first evacuation path borehole 20. The pumped down gases are frozen out and collected in the cooling trap 66. Thus, the throttle nozzle 40 in the second evacuation path effects a gentle, uniform evaporation of the liquid, as well as a gradual build up of the vacuum, it being noted that without such throttle the substance film on the liquid in the reaction vessel would be impaired due to the rapid removal of the liquid.

When the substance film in the reaction vessel is fully surfaced dried, the main shutoff valve 24 is opened, hence opening the first evacuation path. The larger diameter of the borehole 14 and borehole 20 with respect to the second evacuation path effects a removal of the remaining solvent residues from the reaction vessel and produces a fine vacuum. Additionally, the boreholes of the second evacuation path are simultaneously evacuated and hence cleaned of solvent residues so that deposition during repeated reaction cycles are not accumulated in either of the evacuation paths.

It is noted, that the instant invention enables a continuous transfer from prevacuum to fine vacuum with only a single vacuum pump being required. Such continuous transfer prevents damage to the substance film which often occurs when discontinuous pressure changes occur at the moment that the shift from the prevacuum to the fine vacuum is effected. Additionally, positioning a first vacuum measuring tube in the second evacuation path between the throttling point and the auxiliary shuttling valve permits the measurement of the vacuum in the reaction vessel when the shutoff valves are closed. The use of a second vacuum measuring tube disposed in the second evacuation path downstream from the auxiliary shutoff valve is particularly adapted to measure the vacuum when the shutoff valves are closed on the upstream side of the vacuum pump, thereby resulting in the vacuum in the reaction vessel and the vacuum produced directly by the pump being separately monitored. Such a feature not only renders possible a rapid detection of problem sources, but furthermore permits conclusions to be made respecting the reaction procedures in the reaction vessel. Furthermore, because prior evacuation devices have utilized vacuum measuring tubes directly secured to the reaction vessel, early filling of the vacuum measuring tubes and hence contamination of the substance film occurs. Nevertheless, such filling and contamination is substantially eliminated by the joining of the vacuum measuring tubes to the block, hence allowing more accurate measuring results by the vacuum measuring tubes. The block is preferably made from corrosionproof material to protect same against very aggressive substances which are occasionally used during the reaction.

Additionally, improved efficiency and extended service life is provided to the pump by the utilization of the aforementioned and described cooling trap. The cooling traps eliminate the problems caused by the good sized quantities of solvent drawn off by suction during the course of the evacuation of the reaction vessel. Therefore the cooling traps must be of dimensions to receive a sufficient quantity of solvent. The cooling traps can be formed as U-tubes with flow-through joints on the U-shank ends to thereby allow same to be fitted with standard flanges for mounting to the block and vacuum pump. Additionally, the enlarging of the walls on the inside by the indents 72 formed therein further enhances the effectiveness of the cooling function.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An evacuation device adapted to be connected to a single vacuum pump comprising a block, said block defining a first cross-section conduit forming a first vacuum path, a first downstream end of said conduit forming a first opening in said block, said first opening being adapted to be connected to a single vacuum pump, and said upstream end of said conduit defining a second opening in said block, said second opening being adapted to be connected to a vessel to be evacuated, said first conduit including a shut-off valve disposed therein, a second conduit formed in said block having a smaller cross-section than said first conduit, said first and second ends of said second conduit respectively intersecting said first conduit on the upstream and downstream sides of said shut-off valve to effect a bridging thereof and define a further vacuum path, and throttle means disposed in said further vacuum path, said further vacuum path and said throttle means disposed therein being constructed and arranged to induce a prevacuum between said first and second openings in said block in response to the closing of said shut-off valve disposed in said first vacuum path when the first opening in said block is connected to a vacuum pump.

2. An evacuation device as claimed in claim 1, wherein said throttle means includes a throttle nozzle.

3. An evacuation device as claimed in claim 1, said further evacuation path including an auxiliary shut-off valve disposed therein.

4. An evacuation device as claimed in claim 3, wherein said block includes third and fourth conduits formed therein, a first end of said third and fourth conduits forming third and fourth openings in said block, said second ends of said third and fourth conduits respectively intersecting said further vacuum path defined by said second conduit upstream and downstream of said auxiliary shut-off valves disposed therein to provide for measuring of the vacuum pressure in the vessel to be evacuated and the vacuum path at the respective third and fourth openings of said block.

5. An evacuation device as claimed in claim 1, wherein said evacuation device includes a cooling trap connected to the downstream end of said first-mentioned evacuation path.

6. An evacuation device as claimed in claim 5, wherein said cooling trap is a U-tube defining shank junction ends, a first junction end being connected to said downstream end of said first mentioned evacuation path.

7. An evacuation device as claimed in claim 6, wherein the inner walls of said U-shaped tube include enlarged indents for increasing the surface area thereof.

* * * * *